United States Patent [19]

Welch, Jr.

[11] 4,014,890
[45] Mar. 29, 1977

[54] PROCESS FOR PREPARING INDOLE DERIVATIVES
[75] Inventor: Willard M. Welch, Jr., Mystic, Conn.
[73] Assignee: Pfizer Inc., New York, N.Y.
[22] Filed: Mar. 23, 1976
[21] Appl. No.: 669,507
[52] U.S. Cl. .................... 260/296 A; 260/315; 260/319.1; 260/326.15; 260/326.16; 260/326.82; 260/295 C; 260/294.8 B; 260/326.31; 260/313.1
[51] Int. Cl.² .................................. C07D 471/04
[58] Field of Search .......... 260/315, 326.31, 319.1, 260/326.15, 326.16, 326.82, 294.8 B, 295 C, 296 A, 313.1

[56] References Cited
UNITED STATES PATENTS
3,535,326  10/1970  Yamamoto et al. ............... 260/315

OTHER PUBLICATIONS
Posvic et al. "J. Org. Chem.," vol. 39 pp. 2575–2580 (1974).

Primary Examiner—Henry R. Jiles
Assistant Examiner—Robert T. Bond
Attorney, Agent, or Firm—Connolly and Hutz

[57] ABSTRACT

Certain indole derivatives, and especially certain 1,2,3,4-tetrahydrocarbazoles, 1,2,3,4-tetrahydro-γ-carbolines and 1,2,3,4-tetrahydropyrrolo-[3,4-b]indoles are prepared by reacting the appropriate phenylhydrazine salt and ketone in the presence of a weakly basic solvent such as pyridine, quinoline, N,N-dimethylaniline, picoline or lutidine at a temperature in the range of about 50° to 180° C.

11 Claims, No Drawings

PROCESS FOR PREPARING INDOLE DERIVATIVES

BACKGROUND OF THE INVENTION

1. Field of the Invention

The invention relates to a novel process for preparing substituted indoles of the general formula:

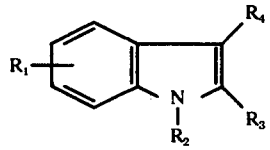

which comprises the reaction of a phenylhydrazine acid addition salt of the formula;

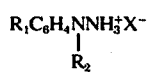

where X is Cl or Br; $R_1$ is a member selected from the group consisting of hydrogen, chloro, bromo, fluoro, methyl and methoxy; $R_2$ is a member selected from the group consisting of hydrogen, alkyl having from one to three carbon atoms, —$C_6H_4R_1$, —$CH_2CH_2NR_7R_8$, and —$CH_2CH_2CH_2NR_7R_8$ wherein $R_7$ and $R_8$ are each alkyl having from one to three carbon atoms; with the proviso that when $R_2$ is —$C_6H_4R_1$, both $R_1$ are the same; with a ketone of the formula

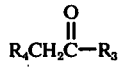

wherein $R_3$ is methyl; $R_4$ is hydrogen; and $R_3$ and $R_4$ when taken together with the

moiety to which they are attached form:

wherein n is an integer from 3 to 6, or

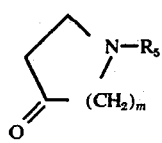

wherein m is 1 or 2;
$R_5$ is —$COOR_6$ or —$SO_2R_6$ and $R_6$ is methyl or ethyl.

Said substituted indoles are old and the prior art teaches their use as pharmaceuticals, pharmaceutical intermediates and for industrial applications as inhibitors in acid pickling of steel and in dry working photographic compositions. U.S. Pat. Nos. 2,541,211; 3,282,942; 3,329,571; 3,925,409, German Pat. No. 930,988 and Belgian Pat. No. 827,451 teach their use as pharmaceuticals and intermediates therefore. U.S. Pat. Nos. 3,329,619; 3,493,376 and Netherlands Pat. No. 6,508,274 teach their use for the above-mentioned industrial applications.

Numbering of tricyclic ring systems discussed herein are as follows:

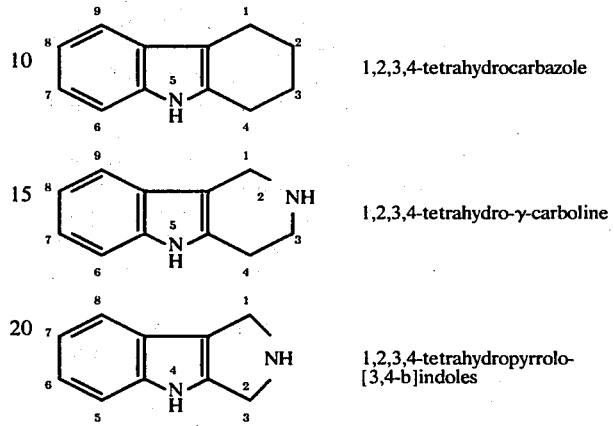

2. Description of the Prior Art

Numerous reports and reviews concerning the preparation of indole derivatives by the general procedure known as the Fischer indole synthesis have appeared over the past 90 years; see for example, the reviews of Robinson, Chem. Rev., 63, 373 (1963) and ibid., 69, 227 (1969), and Brown, in Heterocyclic Compounds, Wiley Interscience Division of John Wiley and Sons, New York, N.Y., 1972, Vol. 25, Part I, W. J. Houlihan, Editor, pp. 246–316, and references cited therein.

Generally, the Fischer indole synthesis is carried out by heating an arylhydrazone in the presence of an appropriate mineral acid, organic acid or Lewis acid. The arylhydrazone undergoes rearrangement followed by cyclization with elimination of ammonia. The arylhydrazone is ordinarily obtained when the appropriate arylhydrazine and carbonyl compound are heated in a suitable organic solvent. e.g. ethanol or acetic acid.

The broad synthetic applicability of the Fischer indole synthesis depends to a large extent upon the selection, often by trial and error, of a suitable acid catalyst which will permit formation of the indole without decomposition of intermediates or the desired product. However, in those cases where the products or intermediates have poor acid stability, the acid catalyzed reaction fails or affords only low yields. Thermal indolization of arylhydrazones has been proposed as a method for preparation of acid sensitive indoles; see e.g., Brown, loc. cit., p. 259; Kelly et. al., Can. Jour. Chem., 43, 296 (1965) and Crooks et. al., Chem. and Ind., 547 (1967). The thermal indole reaction is carried out by heating arylhydrazones in a high boiling solvent such as ethylene glycol, diethylene glycol or tetralin in the absence of acidic catalysts. This method, which has found only limited use, requires prior isolation of a purified arylhydrazone and is carried out at the boiling point of one of the above mentioned solvents, i.e., 198° to 245° C.

The substituted indoles prepared by the process of the invention are known in the art and their utility in pharmaceutical and industrial applications has been previously disclosed. In each of the following references to utility, the substituted indoles disclosed therein are prepared by the above mentioned Fischer indole synthesis by heating an arylhydrazone in an acid medium:

German Pat. No. 930,988; Chem. Abstr. 52, 17288g (1958) teaches the preparation of indoles and tetrahydrocarbazoles, substituted on the benzene ring by methyl or chloro groups and optionally alkylated on the nitrogen atom. It also discloses their chemotherapeutic action against protozoa, especially *Trypanosoma cruzi* and their ability to increase the effect of soporifics.

Methods for preparing and using 2-methyl-indole and 2,5-dimethylindole as inhibitors of metal loss and hydrogen absorption in acid pickling of steel are disclosed in U.S. Pat. No. 3,329,619. The utility of 2,5-dimethylindole and 1,2-dimethylindole in dry working photographic compositions is taught in U.S. Pat. No. 3,493,376, and in Netherlands Pat. No. 6,508,274; *Chem. Abstr.* 64, 1878b (1966), respectively.

U.S. Pat. No. 2,541,211 teaches the preparation of compounds of the formula RAB where R is 1,2,3,4-tetrahydro-5-carbazolyl, A is an alkylene radical containing 2 to 5 carbon atoms and B is a dialkylamino group such as $-N(CH_3)_2$ or $-N(C_2H_5)_2$ as well as their use as intermediates for the preparation of antihistamines and antispasmodics.

Indole derivatives of the general formula:

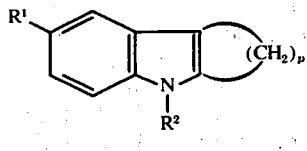

wherein $R^1$ is hydrogen, methyl, fluoro, chloro, nitro and methoxy; $R^2$ is a dialkylaminoalkyl group containing from 4 to 9 carbon atoms and p is an integer from 5 to 13 are disclosed by Rice et. al., *Jour. Med. Chem.*, 7, 313 (1964); U.S. Pat. Nos. 3,282,942 and 3,329,571. They are useful as tranquilizing agents, central nervous system stimulants, appetite depressants and ataractics.

Compounds of the formula:

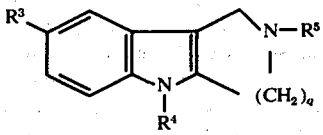

wherein $R^3$ is selected from the group consisting of fluoro, chloro, bromo, methyl and hydrogen; $R^4$ is selected from the group consisting of phenyl and phenyl substituted in the 4-position by fluoro, methoxy, and chloro; and $R^5$ is carbethoxy are intermediates for the preparation of tranquilizing agents. In U.S. Pat. No. 3,925,409 the preparation and use of the compounds in which q is one are disclosed. Preparation and use of the corresponding compounds in which q is two are disclosed in Belgian Pat. No. 827,451 (Derwent No. 68968 W/42).

SUMMARY OF THE INVENTION

A novel modification of the Fischer indole reaction is disclosed for preparing compounds of the formula:

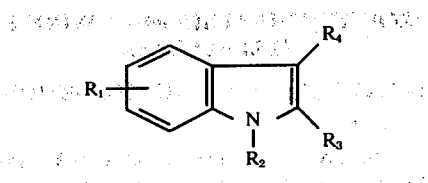

which comprises the reaction of a phenylhydrazine acid addition salt of the formula:

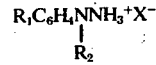

where X is Cl or Br; $R_1$ is a member selected from the group consisting of hydrogen, chloro, bromo, fluoro, methyl and methoxy; $R_2$ is a member selected from the group consisting of hydrogen, alkyl having from one to three carbon atoms, $-C_6H_4R_1$, $-CH_2CH_2NR_7R_8$, and $-CH_2CH_2CH_2NR_7R_8$ wherein $R_7$ and $R_8$ are each alkyl having from one to three carbon atoms; with the proviso that when $R_2$ is $-C_6H_4R_1$, both $R_1$ are the same; with an equimolar amount of a ketone of the formula

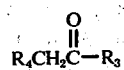

wherein $R_3$ is methyl; $R_4$ is hydrogen; and $R_3$ and $R_4$ when taken together with the

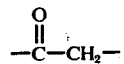

moiety to which they are attached form:

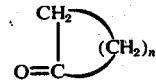

wherein n is an integer from 3 to 6, or

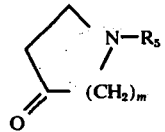

wherein m is 1 or 2;
$R_5$ is $-COOR_6$ or $-SO_2R_6$ and $R_6$ is methyl or ethyl; in the presence of at least an equimolar amount of a weakly basic solvent selected from the group consisting of pyridine, quinoline, N,N-dimethylaniline, picoline and lutidine, at a temperature in the range of about 50° to 180° C. Especially preferred is the process when carried out in the weakly basic solvent pyridine at temperatures in the range of about 70°-115° C.

The process of the invention provides indole derivatives which are themselves useful, for example, as tranquilizing agents, central nervous system stimulants, appetite depressants, ataractics and the above mentioned industrial applications or are useful intermediates for the preparation of valuable compounds such as tranquilizing agents, antihistamines and antispasmodics.

The instant process provides high yields of the above-mentioned indole derivatives under mild conditions directly from the appropriate phenylhydrazine salt and ketone without prior formation of an intermediate phenylhydrazone as is often required when the prior art processes are employed. The present process has further advantages in that no excess of any reagent is necessary or desirable, isolation of product is simplified in that the cooled reaction mixture is ordinarily merely contacted with water to effect precipitation and then isolated by standard techniques. The instant process is especially advantageous when the desired products or intermediates have poor acid stability.

DETAILED DESCRIPTION OF THE INVENTION

While the prior art methods for preparing indole derivatives from phenylhydrazines and ketones require the use of either strongly acidic catalysts or heating at reflux in a high boiling solvent such as ethylene glycol, diethylene glycol or tetralin, the novel process of the present invention provides a method whereby indole derivatives can be readily prepared in high yield under mild conditions by carrying out the reaction in the presence of certain weakly basic solvents. In carrying out the process of the invention, approximately equimolar amounts of the appropriate phenylhydrazine salt (e.g. phenylhydrazine hydrochloride) and ketone are reacted in the presence of at least an equimolar amount of a weakly basic solvent.

By the term "weakly basic solvent" is meant a compound capable of substantially dissolving the reactants of the process of the invention at the reaction temperature employed, and containing a weakly basic group, such as a tertiary nitrogen group, capable of binding protons, which protons may subsequently be donated to stronger bases generated during the reaction, but said compound is otherwise reaction inert, said compound having a $pK_b$ as measured in water at room temperature, in the range of about 7 to 10. Thus, a suitable weakly basic solvent is capable of combining with a strong acid such as hydrogen bromide or hydrogen chloride to attenuate the acid strength of said acid, but is also capable of supplying protons to basic reaction intermediates and byproduct ammonia. Examples of suitable weakly basic solvents are pyridine, quinoline, isoquinoline, N,N-dimethylaniline, N,N-diethylaniline, the picolines, such as 2-picoline, 3-picoline and 4-picoline and the lutidines such as 2,6-lutidine, 2,5-lutidine, 3,5-lutidine and 3,4-lutidine.

Stronger bases, such as triethylamine, N-methylpyrrolidine and N-ethylpiperdine when employed in place of the above mentioned weakly basic solvents, afford little or none of the desired indole products.

While the process of the reaction may be carried out over a wide range of temperature, it is preferred to carry out the reaction at a temperature in the range of about 50° to 180° C. When the weakly basic solvent pyridine is employed, temperatures in the range of about 70° to 115° C. are preferred.

The process of the reaction, when carried out at a temperature within the preferred range of 50° to 180° C., reaches substantial completion within a time which may vary from as little as a few minutes to as much as 24 hours or more. Of course, the time and temperature relationship obeys the normal rules of thermodynamics, i.e., the reaction proceeds at a faster rate at higher temperatures and slower rate at lower temperatures.

While the process of the invention may be carried out with any of the arylhydrazine acid addition salts and ketones which have been found to form arylhydrazones and which react in the well known Fischer indole reaction (see, for example, Brown, in *Heterocyclic Compounds*, Wiley Interscience Division of John Wiley and Sons, New York, N.Y., 1972, Vol. 25, Part I, N. J. Houlihan Editor pp. 227–547, and reference cited therein), I prefer the process of the invention when carried out according to the following reaction outline:

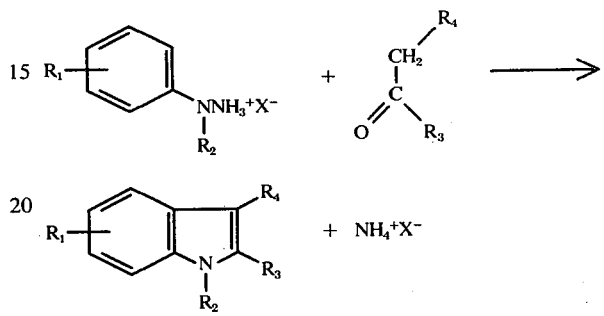

While a molar excess of either of the reactants is ordinarily well tolerated, no advantage has been observed by employing any such excess. Since the amount of either reactant used in excess must then be removed from the products of the reaction, we consequently prefer to use an equimolar amount of the phenylhydrazine acid addition salt and ketone in carrying out the process of the invention in order to simplify the isolation and purification of the products and for reasons of economy.

The above mentioned weakly basic solvent is ordinarily employed in an amount at least equimolar to each of the reactants. However, the process of the invention may be carried out as well in the presence of larger amounts, up to about 10 moles per mole of each reactant, of the weakly basic solvent, and such larger amounts are advantageously employed in some cases to insure substantially complete solution of reactants.

Ordinarily, the reaction, when carried out according to the process of the invention, provides the desired indole derivative and ammonium halide as indicated in the above reaction outline, relatively free of other, undesired by-products. Consequently, the isolation of the desired indole derivative is ordinarily quite simple, often merely requiring the addition of water to precipitate the indole derivative, followed by washing the product with water, e.g., by decantation, followed by filtration and further washing to remove last traces of the weakly basic solvent. The resulting product is often sufficiently pure, but may be further purified, e.g., by crystallization, if desired.

In the above raction outline of the preferred process of the invention, preferred as X are Cl or Br, and Cl is a particularly preferred value of X; preferred $R_1$ are those selected from the group consisting of hydrogen, chloro, bromo, fluoro, methyl and methoxy; $R_2$ is preferably a member selected from the group consisting of hydrogen, alkyl having from one to three carbon atoms, dialkylaminoalkyl of the structures $-CH_2CH_2NR_7R_8$ and $-CH_2CH_2CH_2NR_7R_8$ wherein $R_7$ and $R_8$ are each alkyl having from one to three carbon atoms, and $-C_6H_4R_1$; with the proviso that when $R_2$ is $-C_6H_4R_1$, both $R_1$ are the same. Preferred as $R_3$ in the ketone reactant, R₃COCH₂R₄, is methyl; preferred as R₄ is hydrogen, and when R₃ and R₄ are taken together with the —COCH₂— moiety to which they are attached, they form

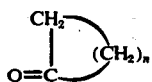

wherein n is an integer from 3 to 6,

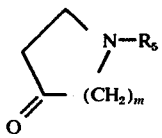

wherein m is 1 or 2; R₅ is —COOR₆ or —SO₂R₆ wherein R₆ is methyl or ethyl. The preferred process of the reaction is carried out in the presence of a weakly basic solvent selected from the group consisting of pyridine, quinoline, N,N-dimethylaniline, picoline and lutidine, at a temperature in the range of about 50° to 180° C. Especially preferred as weakly basic solvent for reasons of economy and efficiency is pyridine. As noted above, when pyridine is employed the preferred temperature for carrying out the process of the reaction is in the range of about 70° to 115° C., the latter being the atmospheric boiling point of pyridine.

As in the prior art methods for carrying out the Fischer indole synthesis, the reaction of the phenylhydrazine and ketone in the present process proceeds via a phenylhydrazone, for example,

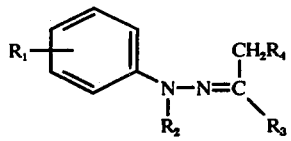

which then rearranges with elimination of ammonia to provide the desired indole product. Of course, an alternate method for carrying out the process of the invention is to start with the above phenylhydrazone and an equimolar amount of strong acid such as hydrogen chloride or hydrogen bromide in the presence of one of the above mentioned weakly basic solvents, such as pyridine. When carried out in this manner the process is considered to be within the scope of the present invention.

The process of the present invention is especially valuable in providing 1,2,3,4-tetrahydro-γ-carbolines and 1,2,3,4-tetrahydropyrrolo-[3,4-b]indoles of the formula

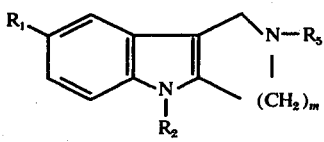

which are intermediates for the synthesis of the tranquilizing agents disclosed in U.S. Pat. No. 3,925,409 and Belgian Pat. No. 827,451. The process for preparing siad intermediates of the above formula comprises the reaction of a phenylhydrazine acid addition salt of the formula

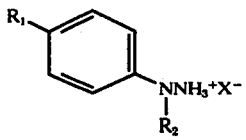

wherein X is Cl or Br; R₁ is a member selected from the group consisting of fluoro, chloro, bromo, methyl and hydrogen; R₂ is a member selected from the group consisting of hydrogen, phenyl and phenyl substituted in the 4-position by a member of the group consisting of fluoro and chloro; with the proviso that when R₂ is said phenyl substituted by fluoro, R₁ is fluoro and when R₂ is said phenyl substituted by chloro, R₁ is chloro; with an equimolar amount of a ketone of the formula

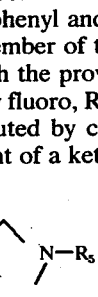

wherein m is 1 or 2; R₅ is —COOR₆ or SO₂R₆ and R₆ is methyl or ethyl; in the presence of at least an equimolar amount of a weakly basic solvent selected from the group consisting of pyridine, quinoline, N,N-dimethylaniline, picoline and lutidine, at a temperature in the range of about 50° to 180° C.

The process of the invention is particularly advantageous in preparation of indole derivatives that give poor yields in the prior art methods for carrying out the Fischer indole synthesis due to instability of the product or an intermediate to strongly acidic catalysts and/or to the high temperatures employed in the thermal method. For example, in the preparation of 2-carbethoxy-1,2,3,4-tetrahydropyrrolo[3,4-b]indoles by the prior art acid catalyzed Fischer indole synthesis yields of the desired products are poor, apparently due to the acid sensitivity of one or more of the intermediates, since 2-carbethoxy-1,2,3,4-tetrahydropyrrolo[3,4-b]indole itself is reasonably stable under the acidic conditions employed. By comparison, when phenylhydrazine hydrochloride and N-carbethoxy-3-pyrrolidinone are reacted according to the process of the invention significantly improved yields of 2-carbethoxy-1,2,3,4-tetrahydropyrrolo[3,4-b]indole are obtained.

The process of the invention is especially valuable when used to provide the following compounds:

2-carbethoxy-1,2,3,4-tetrahydro-γ-carboline, 2-carbethoxy-8-fluoro-1,2,3,4-tetrahydro-γ-carboline,
2-carbethoxy-8-chloro-1,2,3,4-tetrahydro-γ-carboline,
2-carbethoxy-8-bromo-1,2,3,4-tetrahydro-γ-carboline,
2-carbethoxy-8-methyl-1,2,3,4-tetrahydro-γ-carboline,
2-carbethoxy-8-fluoro-5-(p-fluorophenyl)-1,2,3,4-tetrahydro-γ-carboline,
2-carbethoxy-8-chloro-5-(p-chlorophenyl)-1,2,3,4-tetrahydro-γ-carboline,
2-carbethoxy-1,2,3,4-tetrahydropyrrolo[3,4-b]indole,
2-carbethoxy-7-fluoro-1,2,3,4-tetrahydropyrrolo[3,4-b]indole, 2-carbethoxy-7-chloro-1,2,3,4-tetrahydropyrrolo[3,4-b]indole,
2-carbethoxy-7-bromo-1,2,3,4-tetrahydropyrrolo[3,4-b]indole,
2-carbethoxy-7-methyl-1,2,3,4-tetrahydropyrrolo[3,4-b]indole,
2-carbethoxy-7-fluoro-4-(p-fluorophenyl)-1,2,3,4-tetrahydropyrrolo[3,4-b]indole, ,
2-carbethoxy-7chloro-4-(p-chlorophenyl)-1,2,3,4-tetrahydropyrrolo[3,4-b]indole, tetrahydrocarbazole,
8-methoxy-1,2,3,4-tetrahydrocarbazole,
8-chloro-1,2,3,4-tetrahydrocarbazole, Starting materials of the formula

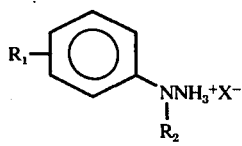

wherein $R_1$ is chloro, bromo, fluoro, methyl and methoxy and $R_2$ is phenyl monosubstituted by chloro, bromo, fluoro, methyl and methoxy, wherein $R_1$ and said phenyl substituents are the same are prepared from the coresponding diphenylamine of the formula, $R_1C_6H_4NHC_6H_4R_1$ by nitrosation and reduction of the nitroso compound with zinc dust as described by Fischer, Ann., 190, 174 (1878). The corresponding compounds, $R_1C_6H_4NHC_6H_4R_1$, are known in the prior art, see for example, Neugebauer et al., Chem. Ber. 104, 886(1971); Burton, J. Chem. Soc., 2246 (1926); and Ritschl, Zeit. Chem., 7, 165 (1967); Chem. Abstr., 67, 15076m (1967).

The following examples are illustrative of the process of the invention, however, many variations are possible without departing from the spirit or scope thereof.

EXAMPLE 1

1,2,3,4,-TETRAHYDROCARBAZOLE

Cyclohexanone (2.0 ml., 0.020 mole), phenylhydrazine hydrochloride (2.88 g., (0.020 mole) and 6.0 ml. of freshly distilled pyridine are combined, heated at reflux (115° C) for 3 hours, then allowed to cool to room temperature and allowed to stir overnight. About 25 ml. of water is added and the precipitated solids are collected by decantation. After washing again with water, the solids are dissolved in a mixture of 20 ml. of ethanol and 5 ml. of water and set aside. The resulting crystals ae collected by filtration, washed with aqueous ethanol and dried to afford 2.65 g. (77.5% of theory) of the title compound, M.P. 119°-120° C. A mixture of the product and an authentic sample of 1,2,3,4-tetrahydrocarbazole also melted a 119°– ° C.

When the above procedure is repeated using an equimolar amount of phenhydrazine hydrobromide in place of phenylhydrazine hydrochloride, the title compound is obtained in a like manner.

When 3.76 g. (0.020 mole) of cyclohexanone phenylhydrazone is heated at reflux for 3 hours in 6.0 ml. of dry pyridine containing 0.020 mole of anhydrous hydrogen chloride, 1,2,3,4-tetrahydrocarbazole is obtained in the same manner.

EXAMPLE 2

8-Methoxy-1,2,3,4tetrahydrocarbazole

4-Methoxyphenylhydrazine hydrochloride (3,49 g., 0.020 mole ), cyclohexanone (2 ml., 0.020 mole) and 6 ml. of dry pryridine are heated at reflux for one hour, cooled and poured into water. The precipitated solid is collected by filtration, dissolved in ethanol and carbon treated. Water was added to the decolorized solution to the cloud point. The product was collected in two crops, M.P. 95°–97° C. Total yield, 3.1 g., 77%.

Anal. Calc'd for $C_{13}H_{15}ON$ (percent): C, 77.58; H, 7.51; N, 6.96; Found: C,77.46; H, 7,56; N, 6.99.

When the above process is carried out in the same manner except that an equal volume of 2-picoline is used in place of pyridine and the reaction mixture is maintained at 50° C. for 24 hours, 8-methoxy-1,2,3,4-tetrahydrocarbazole is also obtained.

Example 3

8-Chloro-1,2,3,4-tetrahydrocarbazole p-Chlorophenylhydrazine hydrochloride (1.79 g., 0.010 mole) is added to a solution of 1.0 ml. (0.010 mole ) cyclohexanone and 3.0 ml. pyridine. The resulting mixture is heated under nitrogen at reflux for 4 hours, cooled to room temperature and water added to precipitate the product. After crystallization from ethanol-water 1.34 g. of the title compound was obtained, M.P. 144.0°–145.6° C. A second crop of crystals 0.18 g. is obtained from the mother liquor. Total yield, 74%.

Anal. Calc'd for $C_{12}H_{12}NCl$ (percent): C, 70.07; H, 5.88; N, 17.24; Found: C, 70.07; H, 5.89; N, 17.22.

When the above process is repeated but the pyridine employed as solvent is replaced with a like amount of quinoline and the reaction is maintained at 180° C. for 20 minutes, the title compound is likewise obtained.

EXAMPLE 4

Following the procedure of Example 3 but employing m-chlorophenylhydrazine hydrochloride in place of the corresponding para-isomer affords a mixture of 7-chloro-1,2,3,4-tetrahydrocarbazole and 9-chloro-1,2,3,4-tetrahydrocarbazole. The isomers may be separated by conventional methods such as fractional crystallization [(see e.g. von Strandmann et al., J. Med. Chem., 6, 719 (1963) and Warner et al., J. Amer. Chem. Soc., 79, 1675 (1957)] or chromatography [see e.g., Symuszkovicz et al., J. Med. Chem., 9, 527 (1966) and McKay et al., Can. J. Chem., 41, 2585 (1963)].

EXAMPLE 5

When the procedure of Example 1 is repeated but using the appropriate starting materials and solvent in each case, the compounds tabulated below are obtained.

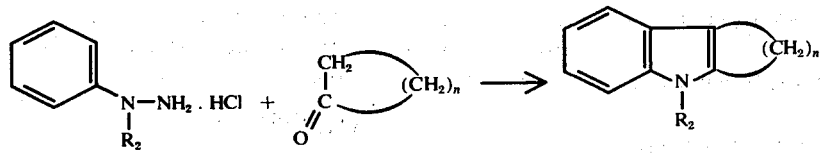

| n | R₂ | Weakly Basic Solvent |
|---|---|---|
| 3 | $CH_3-$ | pyridine |
| 3 | $CH_3CH_2-$ | quinoline |
| 4 | $CH_3(CH_2)_2CH_2-$ | N,N-dimethylaniline |
| 4 | $CH_3(CH_2)_4CH_2-$ | 3-picoline |
| 4 | $(CH_3)_2CHCH_2-$ | 4-picoline |
| 4 | $(CH_3)_2CH(CH_2)_2-CH_2-$ | 2,6-lutidine |
| 5 | $C_6H_5$ | 2,5-lutidine |
| 5 | $CH_3CH_2CH_2$ | 3,4-lutidine |
| 5 | $(CH_3)_2CH-$ | 3,5-lutidine |
| 6 | H | pyridine |
| 6 | H | quinoline |
| 4 | $-CH_2CH_2N(CH_3)_2$ | pyridine |
| 4 | $-CH_2CH_2CH_2N(CH_2CH_3)_2$ | pyridine |

EXAMPLE 6

Following the procedures of previous examples and employing the appropriate starting materials in each case the following compounds are also obtained.

| R₁ | R₂ |
|---|---|
| 6-Cl | H— |
| 6-F— | $C_6H_5$ |
| 7-Br | $CH_3-$ |
| 7-$CH_3-$ | H— |
| 8-F | 4-$FC_6H_4$ |
| 8-$CH_3$ | $CH_3-$ |
| 9-Br | $CH_3-$ |
| 9-$CH_3$ | H— |
| 6-$CH_3O-$ | 2-$CH_3OC_6H_4-$ |
| 8-Cl | 4-$ClC_6H_4$ |
| 8-Br | 4-$BrC_6H_4$ |

EXAMPLE 7

2-Carbethoxy-1,2,3,4-tetrahydro-γ-carboline

Phenylhydrazine hydrochloride (1.44 g., 0.010 mole) is dissolved in 3 ml. of distilled pyridine. The resulting solution is added to 1.71 g. (0.010 mole) of N-carbethoxy-4-piperidone in a 50 ml. reaction vessel equipped with magnetic stirrer, condenser and nitrogen inlet. The resulting mixture is stirred under nitrogen while heating at reflux overnight. The reaction mixture is poured into water and the precipitated solid collected by decantation. The solids were taken up in boiling ethanol, water added until the solution becomes cloudy and crystallization induced by scratching the flask. After cooling, the crystals were filtered, washed with cold aqueous ethanol and air dried to afford 2.40 g. (98.5% of theory) of the title compound, M.P. 127°–129° C. Upon admixture with an authentic sample of 2-carboethoxy-1,2,3,4-tetrahydro-γ-carboline, the melting point was not depressed.

EXAMPLE 8

When the appropriate 4-substituted phenylhydrazine hydrochlorides are employed in place of phenylhydrazine hydrochloride in the procedure of Example 7, the following γ-carbolines are obtained.

| R₁ | M.P. ° C | % Yield |
|---|---|---|
| F— | 168–169 | 47 |
| $CH_3O-$ | 157–159 | 82 |
| Cl— | — | — |
| Br— | — | — |
| $CH_3-$ | — | — |

EXAMPLE 9

2-Carbethoxy-5-phenyl-1,2,3,4-tetrahydro-γ-carboline

N,N-Diphenylhydrazine hydrochloride (2.21 g., 0.010 mole), N-carbethoxy-4-piperidone (1.71 g., 0.010 mole) and dry pyridine, 3 ml., are combined and heated at reflux (115° C.), under a nitrogen atmosphere for 12 hours. The reaction mixture is cooled to room temperature, water added with stirring then decanted, the treatment with water repeated and the solid taken up in ethanol. The solution is carbon treated and the solvent removed by evaporation to afford 2.75 g. of the title compound as an orange oil. Its Nuclear Magnetic Resonance spectrum (CDCl₃) was identical to that of an authentic sample. Yield, 86%. A mass spectrum showed major peaks at the following m/e: 320,291,247,218,169.

When the above procedure is repeated but the reaction mixture is heated at 70° C. for 30 hours the results are substantially the same.

EXAMPLE 10 -Carbethoxy-
2Carbethoxy-8-fluoro-5-(p-fluorophenyl)-1,2,3,4-tetrahydro γ-carboline 1,1-bis-4-Fluorophenylhydrazine hydrochloride, 2.4 g., (0.010 mole) [obtained by nitrosation of 4,4'-difluorodiphenylamine and reduction of the nitroso compound with zinc dust by the method of Fischer, Ann. 190, 174 (1878)] is dissolved in 4 ml. of distilled pyridine and 1.71 g., (0.010 mole) of N-carbethoxy-4-piperidone is added. The resulting mixture is heated at reflux for 5 hours, poured into water and the precipitated solids collected by filtration, and recrystallized to obtain the title compound.

EXAMPLE 11

Following the procedures of the previous examples but employing the appropriate starting materials in each case the following compounds are obtained in like manner.

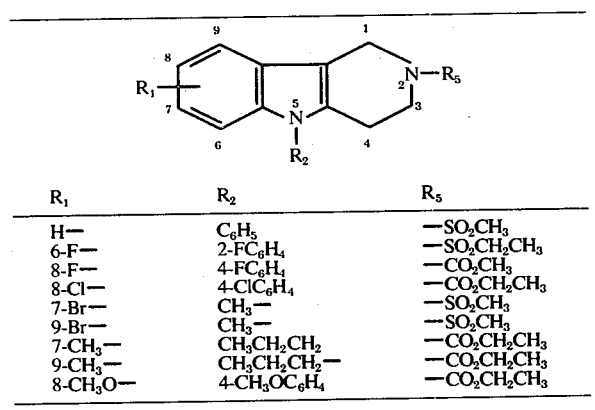

| $R_1$ | $R_2$ | $R_5$ |
|---|---|---|
| H— | $C_6H_5$ | —$SO_2CH_3$ |
| 6-F— | 2-$FC_6H_4$ | —$SO_2CH_2CH_3$ |
| 8-F— | 4-$FC_6H_4$ | —$CO_2CH_3$ |
| 8-Cl— | 4-$ClC_6H_4$ | —$CO_2CH_2CH_3$ |
| 7-Br— | $CH_3$— | —$SO_2CH_3$ |
| 9-Br— | $CH_3$— | —$SO_2CH_3$ |
| 7-$CH_3$— | $CH_3CH_2CH_2$ | —$CO_2CH_2CH_3$ |
| 9-$CH_3$— | $CH_3CH_2CH_2$— | —$CO_2CH_2CH_3$ |
| 8-$CH_3O$— | 4-$CH_3OC_6H_4$ | —$CO_2CH_2CH_3$ |

EXAMPLE 12

2-Carboethoxy-1,2,3,4-tetrahydropyrrolo[3,4-b]indole

Phenylhydrazine hydrochloride (10.0 g., 0.069 mole). N-carbethoxy-3-pyrrolidinone (11.0 g., 0.069 mole) and dry pyridine (11.0 g., 0.138 mole) are combined in a reaction vessel maintained under a nitrogen atmosphere. The resulting mixture is stirred vigorously for 15 minutes at room temperature then heated at 70°-80° C. for 20 minutes. The heat is removed and the reaction mixture, which had turned a deep red color and then thickened during the heating period, is allowed to cool to room temperature. After stirring for an additional 15 minutes at room temperature, the precipitated solid is collected by filtration, washed with benzene and dried to afford 7.35g. of the title compound, M.P. 191°-194° C.

The mother liquor was washed with 100 ml. of water, three 20 ml. portions of 1N hydrochloric acid, once with 40 ml. of saturated sodium bicarbonate solution, and once with saturated sodium chloride solution and finally dried over anhydrous sodium sulfate. The dried solution was then carbon treated (¼ teaspoon of Darco G-60), gravity filtered and the filtrate evaporated to afford a dark oil. Upon slurrying the oil with 10 ml. of cold acetonitrile and filtering an additional 1.30g. of product was obtained, M.P. 193°-196° C.

EXAMPLE 13

When N-carbethoxy-3-pyrrolidinone phenylhydrazone was reacted in refluxing ethanol in the presence of various strong acid acid catalysts such as 85% phosphoric acid, concentrated sulfuric acid and anhydrous zinc chloride, the best yield of 2-carbethoxy-1,2,3,4-tetrahydropyrrolo[3,4-b]indole obtained was 10% of theory. The above phenylhydrazone (M.P. 138° C.) was obtained by reacting equimolar amounts of phenylhydrazine hydrochloride and N-carbethoxypyrrolidinone in refluxing ethanol. The phenylhydrazone is isolated by neutralizing the cooled reaction mixture with potassium carbonate, diluting with water, filtering and drying.

EXAMPLE 14

By using the appropriate starting materials and following the procedure of Example 12, the following compounds are likewise obtained.

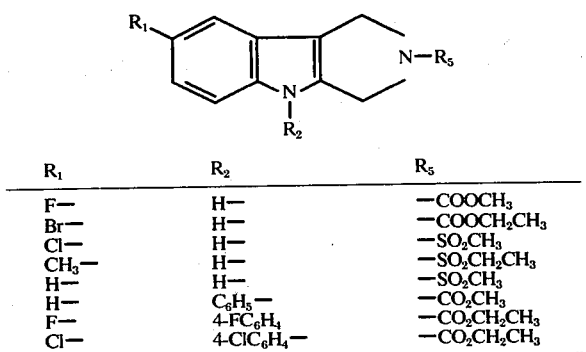

| $R_1$ | $R_2$ | $R_5$ |
|---|---|---|
| F— | H— | —$COOCH_3$ |
| Br— | H— | —$COOCH_2CH_3$ |
| Cl— | H— | —$SO_2CH_3$ |
| $CH_3$— | H— | —$SO_2CH_2CH_3$ |
| H— | H— | —$SO_2CH_3$ |
| H— | $C_6H_5$— | —$CO_2CH_3$ |
| F— | 4-$FC_6H_4$ | —$CO_2CH_2CH_3$ |
| Cl— | 4-$ClC_6H_4$— | —$CO_2CH_2CH_3$ |

EXAMPLE 15

The following substituted indoles are obtained in like manner:

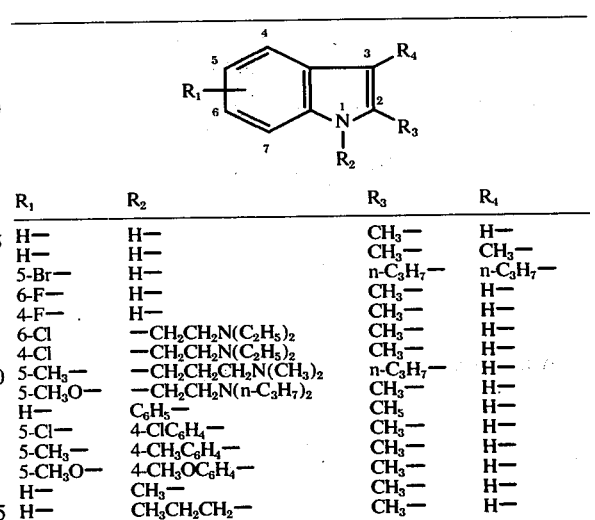

| $R_1$ | $R_2$ | $R_3$ | $R_4$ |
|---|---|---|---|
| H— | H— | $CH_3$— | H— |
| H— | H— | $CH_3$— | $CH_3$— |
| 5-Br— | H— | n-$C_3H_7$— | n-$C_3H_7$— |
| 6-F— | H— | $CH_3$— | H— |
| 4-F— | H— | $CH_3$— | H— |
| 6-Cl | —$CH_2CH_2N(C_2H_5)_2$ | $CH_3$— | H— |
| 4-Cl | —$CH_2CH_2N(C_2H_5)_2$ | $CH_3$— | H— |
| 5-$CH_3$— | —$CH_2CH_2CH_2N(CH_3)_2$ | n-$C_3H_7$— | H— |
| 5-$CH_3O$— | —$CH_2CH_2N(n-C_3H_7)_2$ | $CH_3$— | H— |
| H— | $C_6H_5$— | $CH_3$ | H— |
| 5-Cl— | 4-$ClC_6H_4$— | $CH_3$— | H— |
| 5-$CH_3$— | 4-$CH_3C_6H_4$— | $CH_3$— | H— |
| 5-$CH_3O$— | 4-$CH_3OC_6H_4$— | $CH_3$— | H— |
| H— | $CH_3$— | $CH_3$— | H— |
| H— | $CH_3CH_2CH_2$— | $CH_3$— | H— |

What is claimed is:

1. The process for preparing compounds of the formula:

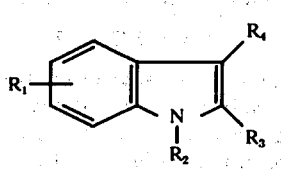

which comprises reacting a phenylhydrazine acid addition salt of the formula:

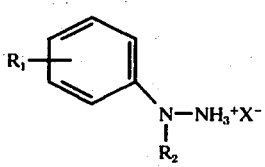

where
X is Cl or Br;
$R_1$ is a member selected from the group consisting of hydrogen, chloro, bromo, fluoro, methyl and methoxy;
$R_2$ is a member selected from the group consisting of hydrogen, alkyl having from one to three carbon atoms, $-C_6H_4R_1$, $-CH_2CH_2NR_7R_8$ and $-CH_2CH_2-CH_2NR_7R_8$ wherein $R_7$ and $R_8$ are each alkyl having from one to three carbon atoms;
with the proviso that when $R_2$ is $-C_6H_4R_1$, both $R_1$ are the same; with an equimolar amount of a ketone of the formula:

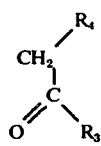

wherein
$R_3$ is methyl;
$R_4$ is hydrogen;
and $R_3$ and $R_4$ when taken together with the

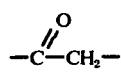

moiety to which they ae attached, form

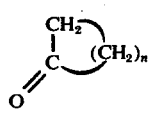

wherein n is an integer from 3 to 6, or

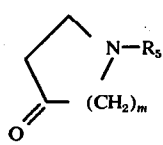

wherein m is 1 or 2; $R_5$ is $-COOR_6$ or $-SO_2R_6$ and $R_6$ is methyl or ethyl; in the presence of at least an equimolar amount of a weakly basic solvent selected from the group consisting of pyridine, quinoline, N,N-dimethylaniline, picoline and lutidine, at a temperature in the range of about 50° to 180° C.

2. The process for preparing compounds of the formula:

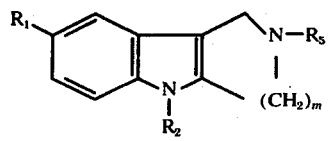

which comprises the reaction of a phenylhydrazine acid addition salt of the formula:

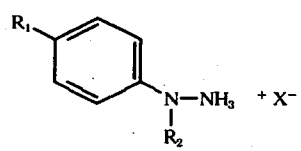

wherein
X is Cl or Br;
$R_1$ is a member selected from the group consisting of fluoro, chloro, bromo, methyl and hydrogen;
$R_2$ is a member selected from the group consisting of hydrogen, phenyl and phenyl substituted in the 4position by a member of the group consisting of fluoro and chloro; with the proviso that when $R_2$ is said phenyl substituted by fluoro, $R_1$ is fluoro and when $R_2$ is said phenyl substituted by chloro, $R_1$ is chloro;
with an equimolar amount of a ketone of the formula:

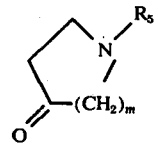

wherein
m is 1 or 2;
$R_5$ is $-COOR_6$ or $-SO_2R_6$
and $R_6$ is methyl or ethyl;
in the presence of at least an equimolar amount of a weakly basic solvent selected from the group consisting of pyridine, quinoline, N,N-dimethylanaline, picoline, and lutidine, at a temperature in the range of about 50°to 180° C.

3. The process according to claim 2 wherein m is 2; $R_1$ is selected from the group consisting of fluoro, chloro, bromo, methyl ad hydrogen; $R_2$ is hydrogen; and $R_5$ is $-COOC_2H_5$.

4. The process according to claim 2 wherein m is 2, $R_1$ is fluoro, $R_2$ is 4-flurophenyl and $R_5$ is $-COOC_2H_5$, 5. The process according to claim 2 wherein m is 2, $R_1$ is chloro, $R_2$ is 4-chlorophenyl and $R_5$ is $-COOC_2H_5$.

6. The process according to claim 2 wherein m is 1 $R_1$ is selected from the group consisting of fluoro, chloro, bromo, methyl and hydrogen; $R_2$ is hydrogen and $R_5$ is —$COOC_2H_5$.

7. The process according to claim 2 wherein $m$ is 1, $R_1$ is fluoro, $R_2$ is 4-fluorophenyl and $R_5$ is —$COOC_2H_5$.

8. The process according to claim 2 wherein $m$ is 1, $R_1$ is chloro, $R_2$ is 4-chlorophenyl and $R_5$ is —$COOC_2H_5$.

9. The process according to claim 1 wherein X is Cl.

10. The process according to claim 1 wherein said weakly basic solvent is pyridine.

11. The process according to claim 10 wherein said reaction is carried out at a temperature in the range of about 70° to 115° C.

* * * * *

UNITED STATES PATENT OFFICE
CERTIFICATE OF CORRECTION

PATENT NO. : 4,014,890
DATED : March 29, 1977
INVENTOR(S) : Willard M. Welch, Jr.

It is certified that error appears in the above-identified patent and that said Letters Patent are hereby corrected as shown below:

Column 9, line 31, "coresponding" should read -- corresponding --

Column 10, line 12, "pryridine" should read -- pyridine --

Column 13, line 7, delete "-Carbethoxy-".

Column 13, line 8, "2Carbethoxy" should read -- 2-Carbethoxy --.

Column 16, line 34, "4position" should read --4-position --.

Column 16, line 55, "-dimethylanaline" should read --dimethylaniline -- .

Column 16, line 60, "ad" should read -- and --.

Column 16, line 63, "flurophenyl" should read -- fluorophenyl --

Column 16, line 67, "1 $R_1$" should read -- 1;$R_1$ --.

Signed and Sealed this fifth Day of July 1977

[SEAL]

Attest:

RUTH C. MASON
Attesting Officer

C. MARSHALL DANN
Commissioner of Patents and Trademarks